(12) United States Patent
Schreibeis et al.

(10) Patent No.: US 10,451,529 B2
(45) Date of Patent: Oct. 22, 2019

(54) CRYOGENIC SYSTEMS AND METHODS

(71) Applicant: Montana Instruments Corporation, Bozeman, MT (US)

(72) Inventors: Caleb Schreibeis, Bozeman, MT (US); Ben Linkenhoker, Bozeman, MT (US); Luke Mauritsen, Belgrade, MT (US)

(73) Assignee: Montana Instruments Corporation, Bozeman, MT (US)

( * ) Notice: Subject to any disclaimer, the term of this patent is extended or adjusted under 35 U.S.C. 154(b) by 299 days.

(21) Appl. No.: 15/456,064

(22) Filed: Mar. 10, 2017

(65) Prior Publication Data

US 2017/0261413 A1    Sep. 14, 2017

Related U.S. Application Data

(60) Provisional application No. 62/307,303, filed on Mar. 11, 2016.

(51) Int. Cl.
*F25D 3/10* (2006.01)
*G01N 1/42* (2006.01)
(Continued)

(52) U.S. Cl.
CPC ............. *G01N 1/42* (2013.01); *F16F 15/06* (2013.01); *F17C 3/085* (2013.01); *F25D 3/10* (2013.01);
(Continued)

(58) Field of Classification Search
CPC ...... F25D 19/006; F25D 3/10; F25B 2500/13; G01N 1/42
See application file for complete search history.

(56) References Cited

U.S. PATENT DOCUMENTS 3,894,403 A    7/1975    Longsworth
3,929,516 A    12/1975   Cheskis et al.
(Continued)

FOREIGN PATENT DOCUMENTS

CN    103901232    7/2014
EP    0619440      10/1994
(Continued)

OTHER PUBLICATIONS

Mueller Copper 1100 (Electrolytic Tough Pitch Snow Pitch Copper), Alloy Digest, 1983, 2 pages.
(Continued)

*Primary Examiner* — Brian M King
(74) *Attorney, Agent, or Firm* — Wells St. John P.S.

(57) ABSTRACT

Cryogenic sample analysis systems are provided that can include: a system housing in direct physical contact with an environment about the system; a sample platform within the system housing; and a resonance frequency insulating assembly operatively engaged between the sample platform and the housing. Cryogenic sample analysis systems are also provided that can include: a system housing in direct physical contact with an environment supporting and surrounding the system; a sample platform within the system and operationally coupled to a coldhead of the system; and an insulating assembly operatively engaged between resonance frequencies generated by the environment and/or the coldhead, the insulating assembly comprising a suspended mass.

9 Claims, 6 Drawing Sheets

(51) Int. Cl.
- *G01N 21/25* (2006.01)
- *F16F 15/06* (2006.01)
- *F17C 3/08* (2006.01)
- *F25D 19/00* (2006.01)

(52) U.S. Cl.
CPC ......... *F25D 19/006* (2013.01); *G01N 21/255* (2013.01)

(56) References Cited

U.S. PATENT DOCUMENTS

| | | |
|---|---|---|
| 4,161,747 A | 7/1979 | Jennings |
| 4,745,761 A | 5/1988 | Bazaj et al. |
| 4,854,131 A | 8/1989 | Sakitani et al. |
| 4,869,068 A | 9/1989 | Van Vloten |
| 4,968,663 A | 11/1990 | Whang |
| 5,327,733 A | 7/1994 | Boolchand et al. |
| 5,349,823 A * | 9/1994 | Solomon ............. F02G 1/0435 257/E23.096 |
| 5,410,910 A | 5/1995 | Somlyo et al. |
| 5,613,367 A | 3/1997 | Chen |
| 5,628,195 A * | 5/1997 | Hill ...................... F17C 13/006 62/295 |
| 5,737,927 A | 4/1998 | Takahashi et al. |
| 5,749,243 A | 5/1998 | Lester |
| 6,005,964 A | 12/1999 | Reid et al. |
| 6,196,005 B1 * | 3/2001 | Stautner ................. F17C 3/085 62/6 |
| 7,932,733 B2 | 4/2011 | Sasajima et al. |
| 8,114,321 B2 | 2/2012 | Johnson |
| 8,746,008 B1 * | 6/2014 | Mauritsen ............... F25B 1/10 62/510 |
| 8,756,941 B2 | 6/2014 | Snow et al. |
| 9,303,914 B2 | 4/2016 | Mauritsen et al. |
| 9,821,421 B2 | 11/2017 | Mauritsen et al. |
| 2005/0126187 A1 | 6/2005 | Li et al. |
| 2005/0204748 A1 | 9/2005 | Yamanaka et al. |
| 2006/0148276 A1 | 7/2006 | Renaudin |
| 2007/0234751 A1 | 10/2007 | Nagamune |
| 2007/0278719 A1 | 12/2007 | Adachi et al. |
| 2009/0224788 A1 | 9/2009 | Sasajima et al. |
| 2009/0272127 A1 | 11/2009 | Radovinsky et al. |
| 2010/0050661 A1 * | 3/2010 | Snow ...................... F25B 9/14 62/51.1 |
| 2014/0248649 A1 | 9/2014 | Mayer et al. |
| 2015/0248002 A1 | 9/2015 | Ingersoll et al. |
| 2017/0168121 A1 | 6/2017 | Yu et al. |
| 2017/0323764 A1 | 11/2017 | Muto et al. |

FOREIGN PATENT DOCUMENTS

| | | |
|---|---|---|
| JP | 05059503 A | 3/1993 |
| JP | H08-341487 A | 12/1994 |

OTHER PUBLICATIONS

Snow, U.S. Appl. No. 61/136,138, filed Aug. 14, 2009, titled "Apparatus(es) & Methods for Improving Vibration Isolation, Thermal Dampening, Optical Access in Cryogenic Refridgerators", 18 pages.

White, G.K. "The Thermal and Electrical Conductivity of Copper at Low Temperatures", 1953, pp. 398-404.

* cited by examiner

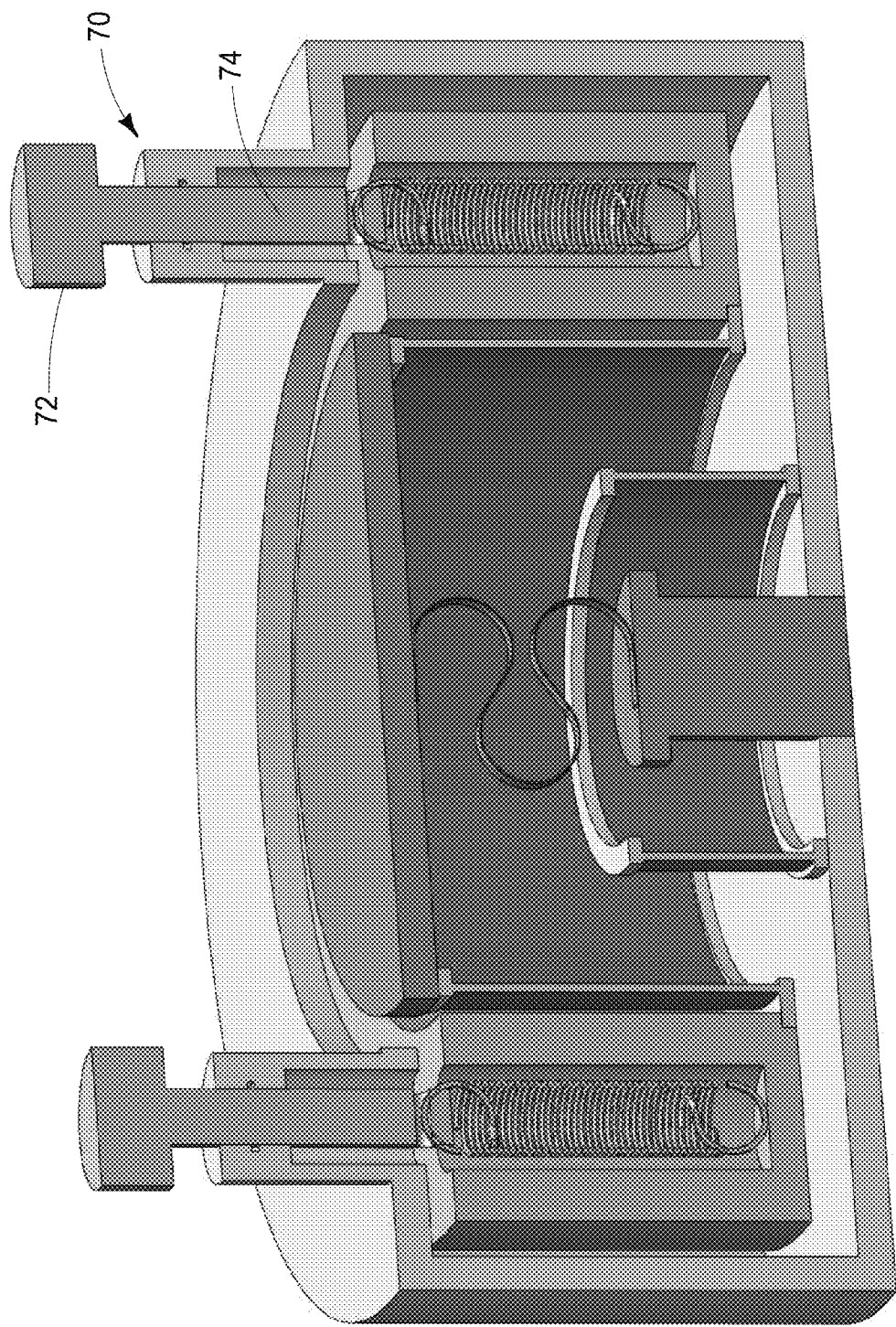

CRYOGENIC SYSTEMS AND METHODS

CROSS REFERENCE TO RELATED APPLICATION

This application claims priority to U.S. provisional patent application Ser. No. 62/307,303 which was filed Mar. 11, 2016, entitled "Cryogenic Systems and Methods", the entirety of which is incorporated by reference herein.

TECHNICAL FIELD

The present disclosure relates to cryogenic systems and methods. Particular embodiments of the disclosure relate to sample stage configurations in cryogenic systems and methods of staging samples.

BACKGROUND

The present invention relates to systems and methods for cryogenic research. More particularly, the present invention relates to systems and methods for microscopy and spectroscopy of cryocooled samples.

Problems associated with low temperature microscopy are many. The cooling systems cause sample vibration; maintaining a constant temperature of the sample is likewise a challenge. There have been attempts to address these problems, yet no solution provides a reliable system that supports a sample without vibration and maintaining sample temperature.

A need remains for a system that effectively isolates a cryocooled sample from vibration of the cooling system while maintaining the sample at a steady temperature.

SUMMARY OF THE DISCLOSURE

Cryogenic sample analysis systems are provided that can include: a system housing in direct physical contact with an environment about the system; a sample platform within the system housing; and a resonance frequency insulating assembly operatively engaged between the sample platform and the housing.

Cryogenic sample analysis systems are also provided that can include: a system housing in direct physical contact with an environment supporting and surrounding the system; a sample platform within the system and operationally coupled to a coldhead of the system; and an insulating assembly operatively engaged between resonance frequencies generated by the environment and/or the coldhead, the insulating assembly comprising a suspended mass.

Methods for analyzing a cryogenically cooled sample are provided with the methods including: placing a sample on a sample platform; cryogenically cooling the sample platform and the sample; and insulating both the sample platform and the sample from both external temperatures and resonance frequencies.

DRAWINGS

Features disclosed herein are referenced in the accompanying drawings which illustrate embodiments of the disclosure.

FIG. 7 is a perspective view of another sample support assembly according to another embodiment of the disclosure.

DESCRIPTION

This disclosure is submitted in furtherance of the constitutional purposes of the U.S. Patent Laws "to promote the progress of science and useful arts" (Article 1, Section 8).

Figure 1:
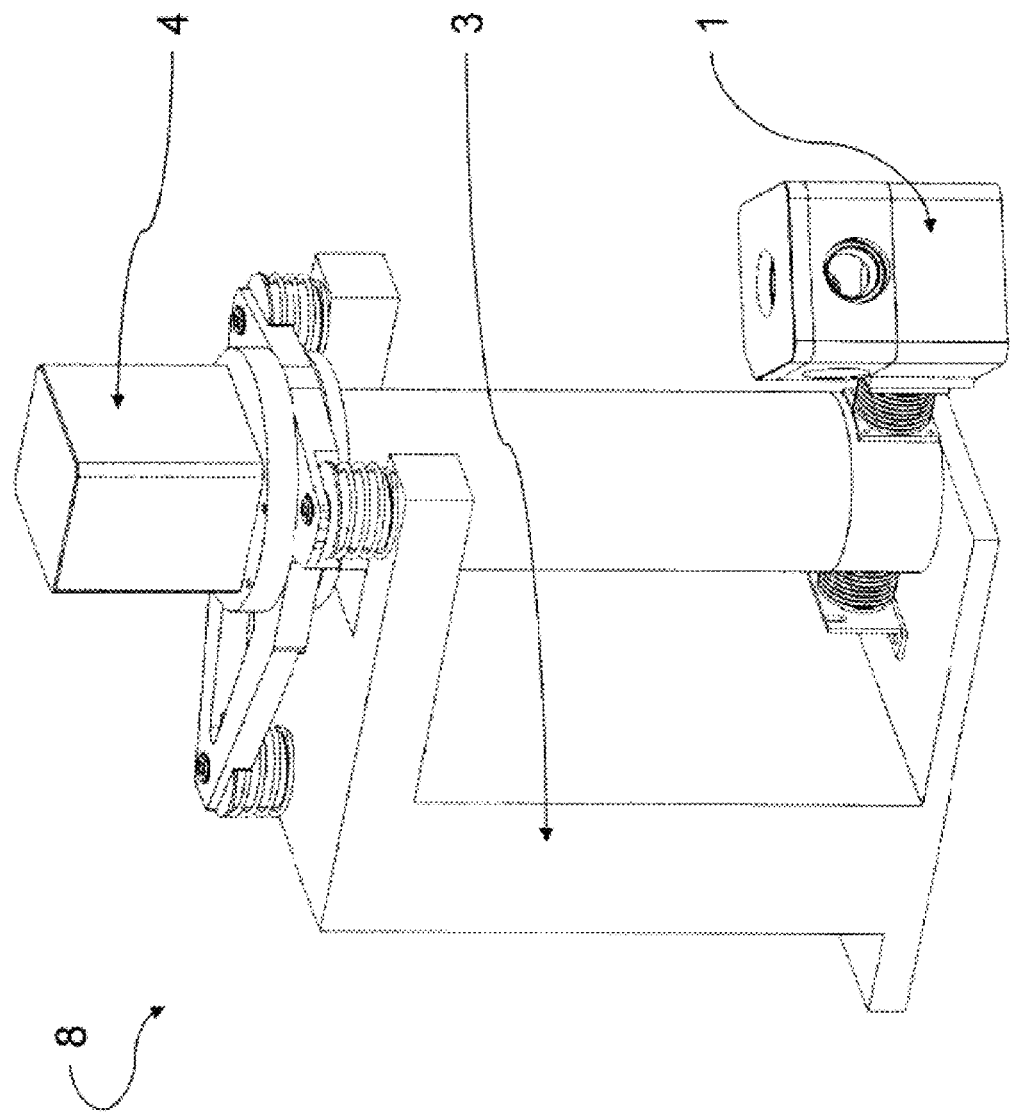
FIG. 1 is a side perspective view of a cryogenic system in accordance with embodiments of the disclosure.

Embodiments of the present disclosure will be described with reference to FIGS. 1-7. Referring first to FIG. 1, an exemplary cryogenic system 8 is depicted. Cryogenic system 8 can be generally configured as described in U.S. Pat. No. 8,746,008 to Mauritsen et al. and entitled, "Low Vibration Cryocooled System for Low Temperature Microscopy and Spectroscopy Applications", the entirety of which is incorporated by reference herein.

Cryogenic system 8 can include a support 3 which supports a closed-cycle cryocooler expander unit 4 which can be operatively aligned with sample housing 1. Unit 4 can be a Sumitomo Heavy Industries RDK-101D cryocooler.

Figure 2:
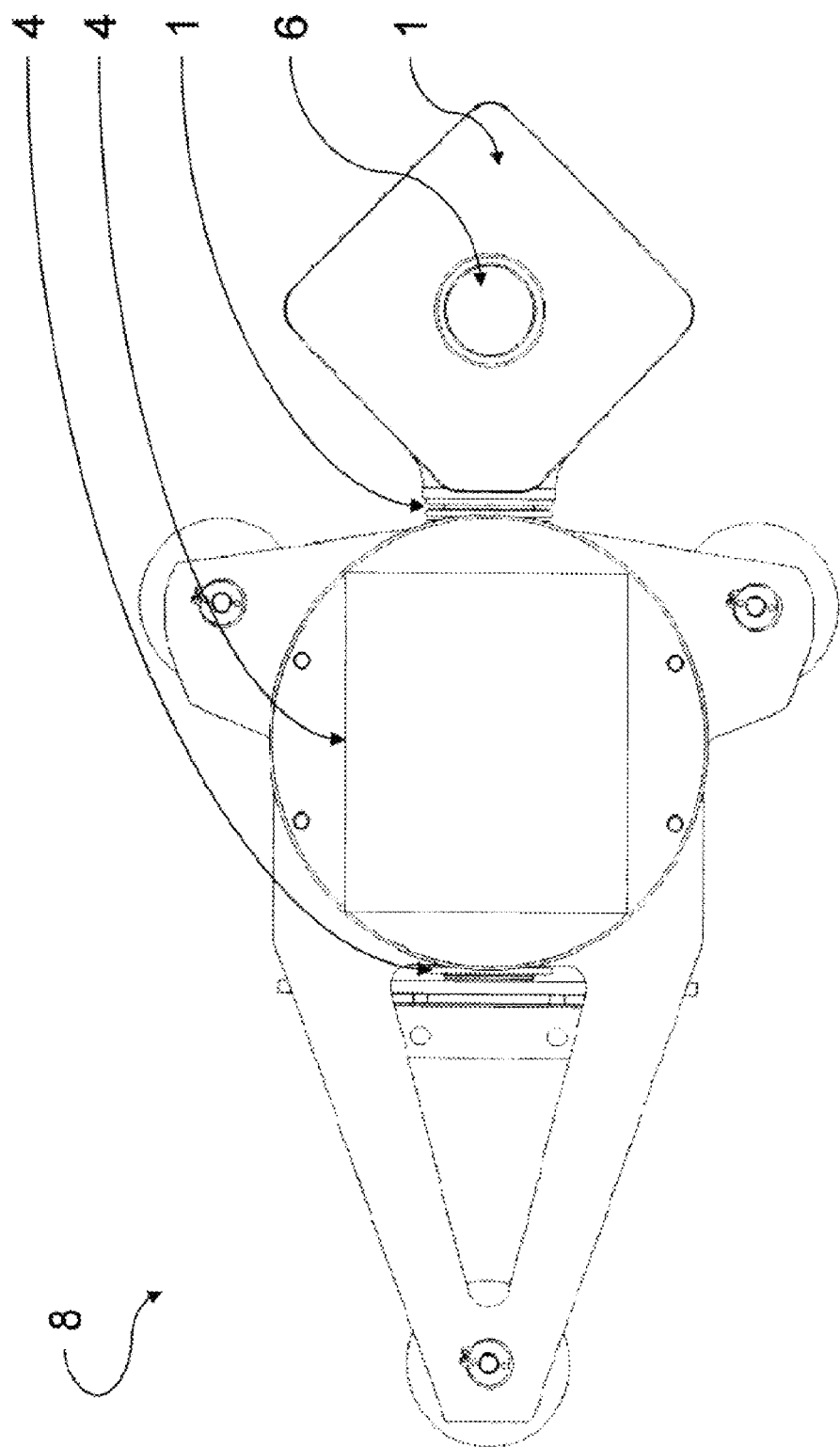
FIG. 2 is a top plan view of the cryogenic system of FIG. 1 according to an embodiment of the disclosure.

Referring next to FIG. 2, spring dampers 5 may be operatively aligned between unit 4 and support 3. Unit 4 can be connected to sample housing 1 and cryogenic system sample support 11 by bellows 2. The diameter of bellows 2 can be in the range from about 0.75 inches to about 3 inches and is more preferably in the range from about 1 inch to about 1.25 inches.

Figure 3:
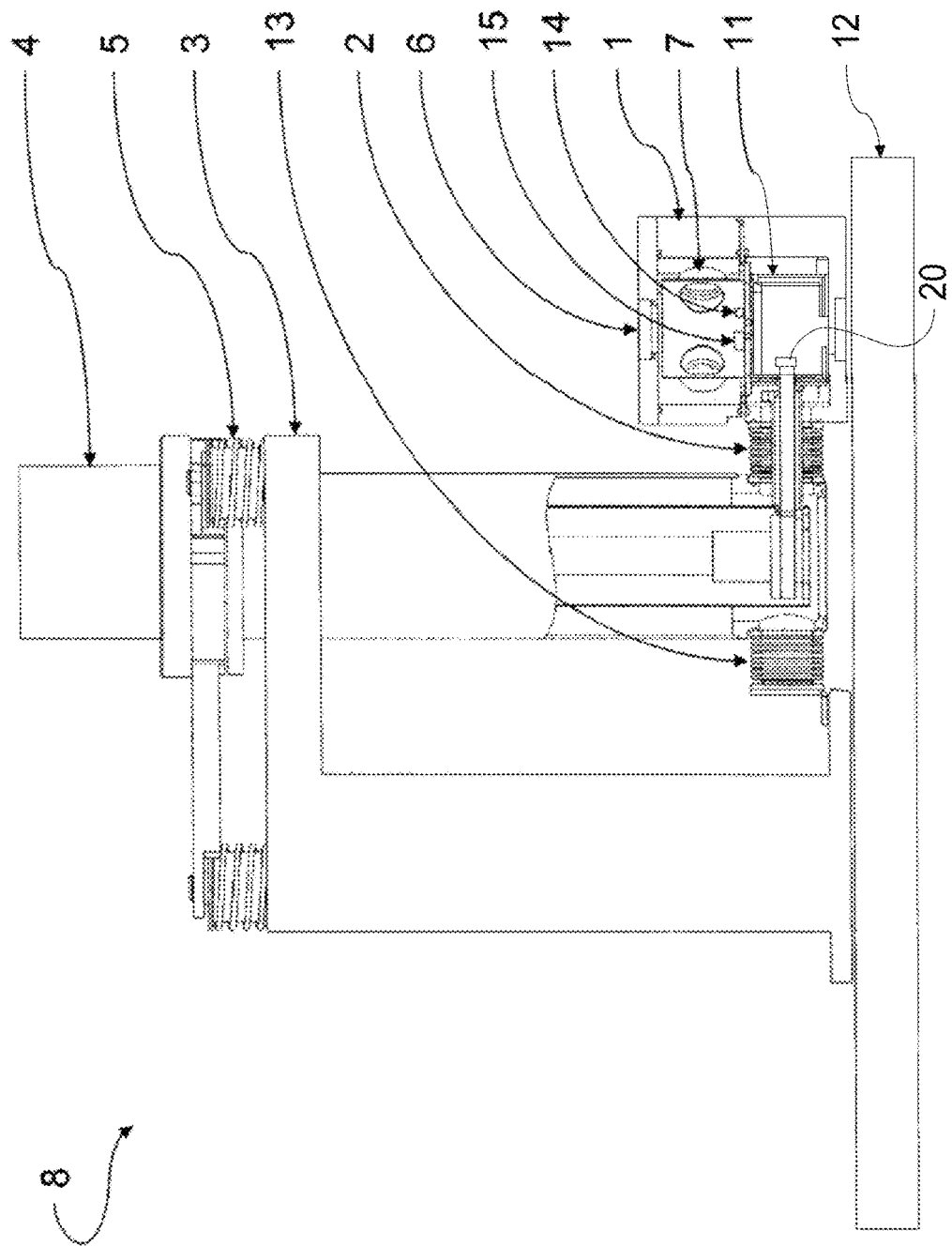
FIG. 3 is a side elevational cutaway view of the cryogenic system of FIG. 1 according to an embodiment of the disclosure.

Referring next to FIG. 3, in typical use, both rigid support 3 and sample housing 1 rest on an optical bench 12 or on another rigid plane. In at least one embodiment, optical bench 12 can be a Newport air isolated table. As shown the system and its housings can be in direct physical contact with the environment about the system. For example, the bench upon which the system rests can in provide vibrations in the form of resonance frequency to the analytical system. Analytical laboratories and associated benches therein, can be less than static due to the presence of analysts in the laboratory. Analysts cannot exist in a mechanical insulative bubble, so resonance frequencies will be generated in their presence. In other examples, the temperature of the air about the system can be substantially different than the desired temperature of a cryocooled sample to be analyzed.

Optical access to the cryocooled sample inside the sample housing 1 is through the top optical access port 6 and/or through the side access ports 7. In accordance with example implementations, the sample is supported by a support assembly 11 which holds the sample in a fixed location relative to the optical bench 12. The cryocooler also can be attached to the rigid support 11 by a separate flexible hermetic sealing bellows 13 that is in alignment with flexible vacuum bellows 2. A temperature sensor 14 and a heater 15 may be operatively associated with sample support assembly 11 near the sample to allow for an adaptive feedback loop to reduce temperature fluctuations. In at least one embodiment, the temperature sensor is a Cernox temperature sensor from Lakeshore Cryogenics Inc.

In more detail, system 8 allows a sample to be cryogenically cooled and rigidly mounted to the optics bench 12 and aligned separately (situated a distance away) from the axis of the cryocooler expander unit 4 such that top access to the sample housing 1 via top access port 6 may be achieved. This unique configuration in which the sample is located off axis from and a distance away from the cryocooler expander unit 4 reduces sample vibration by isolating the sample. The pair of flexible vacuum bellows 2 and 13 which connect the cryocooler expander unit 4 to the sample housing 1 and to the rigid support 3 are preferably aligned along a common axis and opposed to one another such that when there is a differential pressure on the inner and outer surfaces of the bellows 2, there is no net force imposed on the cryocooler expander unit 4.

Cryocooling can be accomplished via a coldhead 20 that can be thermally coupled to the sample platform of support assembly 11. Specifically, the cryocooler can be operated manually until the cryogenic system sample platform has reached a stable temperature near the desired measurement temperature as measured by the temperature sensor 14. At that time the temperature profile of at least one cycle of the cryocooler is recorded. Based on this initial, uncontrolled temperature profile, a profile of heater values which is inversely proportional to the recorded temperature profile is applied using heater 15 synchronously with the cryocooler cycle and adjusted for phase relative to the cryocooler cycle to optimize the temperature minimization.

A second phase of optimization of the heater profile can be obtained by measuring the residual cyclical temperature variation of each value of the heater profile with sensor 14. A correction factor to each value of the heater profile is applied using heater 15 that is proportional to each measured residual value.

A laser, optics and a microscope may be used with system 8 to interrogate and observe a cooled sample, all of which are supported by a common optics bench. Operation of the system can include cooling the cryocooler expander unit 4 to cryogenic temperatures and using the optical apertures 6 and/or 7 for observation of the sample using microscopes or other imaging devices and interrogation of the sample using lasers or other electromagnetic energy propagation devices along with detection of signals returned by the interrogated sample.

Many variations of the disclosure will occur to those skilled in the art. Some variations include an inverted cryocooler expander unit 4 such that it would be located underneath the optics bench 12 and extend up through a hole in the optics bench, or extend up over the edge of the optics bench 12. Other variations call for the cryocooler expander unit 4 being supported by structure separate from the optics bench 12 where the sample housing 1 is located. Additionally, the environment surrounding the sample may be altered or changed by adding a magnetic field, high pressure, RF field, or other types of environmental alterations. All such variations are intended to be within the scope of this disclosure.

Support assembly 11 can be configured to reduce passive and/or active vibration as a mass-biased system. In this configuration, assembly 11 can reduce mechanical energy on a supported mass. Generally, the larger the mass and the softer the springs of spring/mass passive and/or active mechanical filter result in less energy transfer through the isolating filter. By increasing the mass overall isolation performance can improved in the following areas: greater degree of passive and/or active isolation for a given springs stiffness and a greater inertial force when inevitably adding thermal and electrical connections across the filter.

However large masses realize difficulties in a cryogenic environment. Firstly, large masses must typically be cooled to cryogenic temperatures which can take a very long time. Secondly, thermal agility to change temperatures is severely hampered (slowed down) because of such a large heat capacity involved in the system. And lastly, the change in stiffness and performance biasing assembly in mass-biased systems can change dramatically as they experience large swings in temperature.

Support 11 of the present disclosure can eliminate the problems described above. With the use of an effective thermal standoff, a cryogenic system sample platform can be rigidly attached to the isolated mass while still remaining thermally independent. An effective thermal standoff could include any thermal resistive material in the form of any rigid structural shape for example. These systems and methods can provide for a passive and actively isolated cryogenic system sample platform to have a relatively much smaller thermal mass as well as thermal agility, while experiencing the benefits of low acceleration (or high passive isolation) provided by the inertial mass. Also, with the mass and bias assembly at room temperature, the fluctuation of temperature to affect the performance of the spring system is minimized.

In accordance with the systems and methods of the present disclosure, a low resonance frequency can be obtained that can prevent overlap with the most common resonance modes found in a typical laboratory. Sample cool down rates can be increased by isolating the sample platform from the entirety of the sample support assembly. During cool down or maintenance of same, lower accelerations are experienced by relying on the inertia of the large mass of the assembly. The support assembly can allow for the installation of stiffer or thicker thermal links between the cold finger and the sample platform, which can provide faster cool down times. Other stiff connections to the sample platform may also be provided when implementing the sample support assembly of the present disclosure; such connections can include wiring, RF, and/or fiber connections. Using the support assembly of the present disclosure, closed cycle coldheads can be utilized as well.

Figure 4:
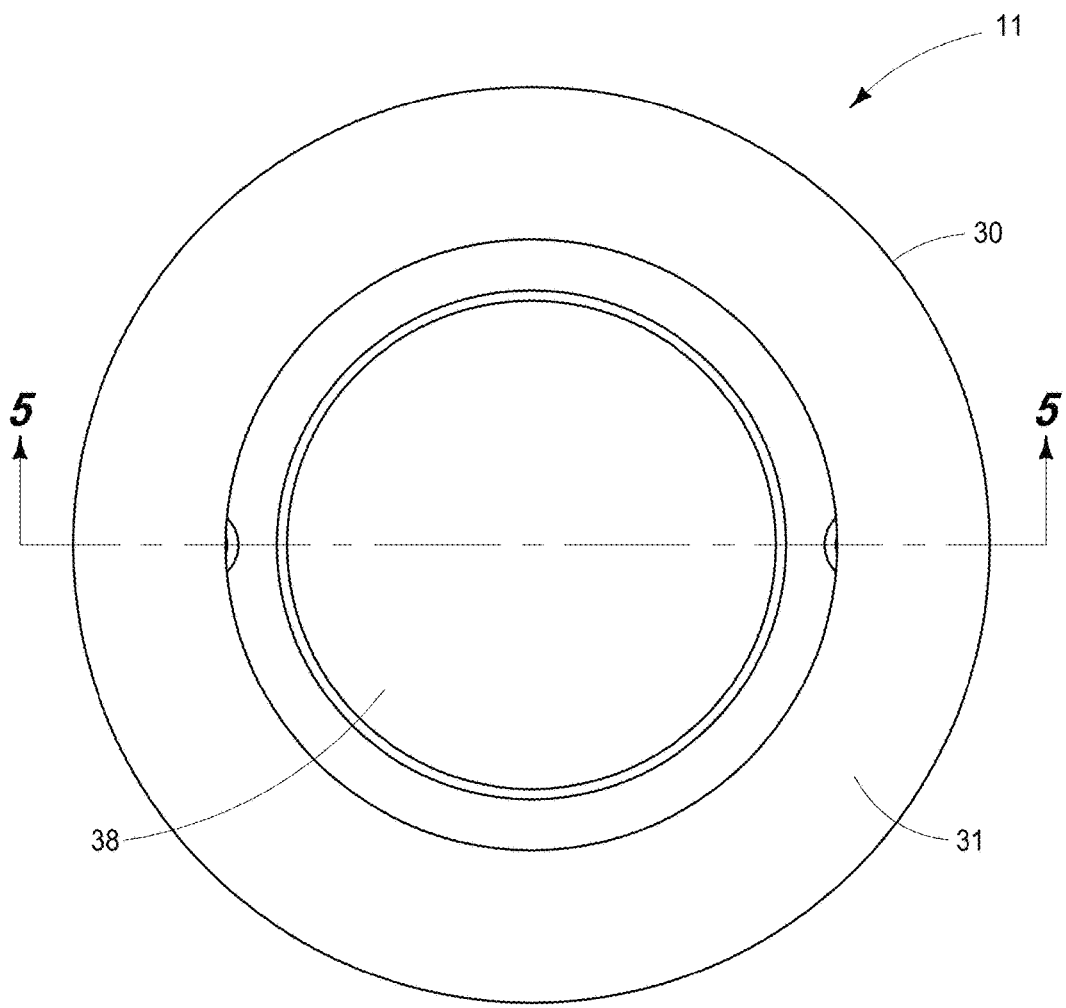
FIG. 4 is a top view of a sample support assembly according to an embodiment of the disclosure.
Figure 5:
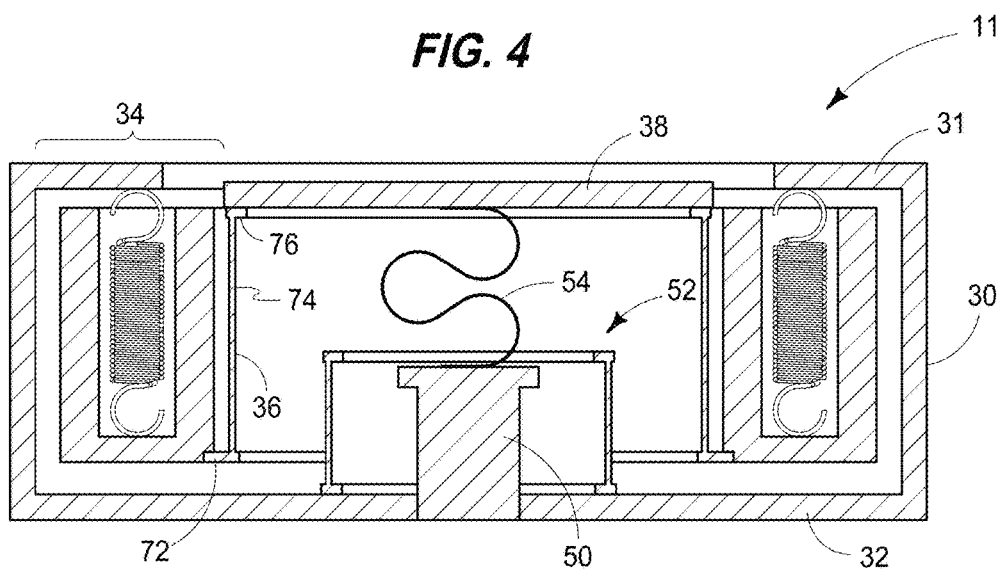
FIG. 5 is a cross section of the sample support assembly of FIG. 4 according to an embodiment of the disclosure.
Figure 6:
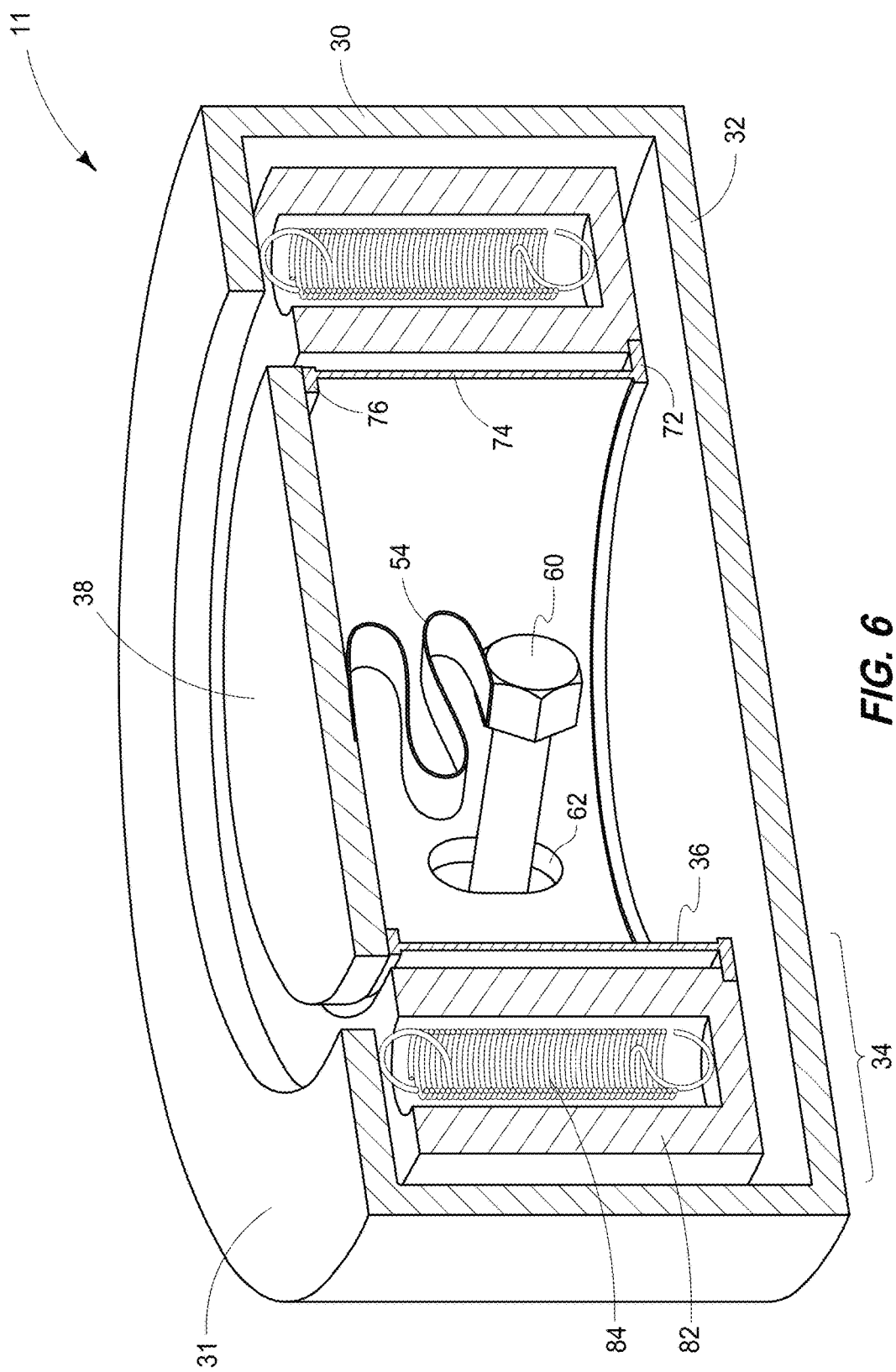
FIG. 6 is a perspective view of the sample support assembly of FIG. 4 according to an embodiment of the disclosure.

Referring next to FIGS. 4-6, embodiments of assembly 11 are depicted. Assembly 11 can include a housing 30 that includes a base 32 and a rim 31. In accordance with example implementations, housing 30 can be a system housing and in direct physical contact with an environment about the system. Housing 30 is not necessarily an exterior portion of the entire system; there may be other portions of the entire system separating assembly 11 from the exterior environment.

Coupled to rim 31 and within housing 30 can be resonance frequency insulating assembly 34 which is coupled to support structure 36. Structure 36 can support sample platform 38 and may be considered a standoff in accordance with example implementations. Standoffs of the present disclosure may be considered a radiation shield and may be considered insulative. In accordance with example implementations, the standoff can be constructed of fiberglass. As shown and according to example implementations, the standoffs of the present disclosure occupy relatively little mass when compared to the large mass of assembly 11.

Base 32 can be in thermal and physical contact with the bench 12, and base 32 as well as rim 31 can be constructed of a solid structure or be multiple pieces aligned to form housing 30.

Resonance frequency insulating assembly 34 can be operatively engaged between sample platform 38 and housing 30. Assembly 34 can include a body 82, such as a weighted member, and a biasing mechanism 84. Body 82 can provide a substantial amount of weight as part of components 34, 36, and 38. This weight in combination with biasing member 84 can provide a floating sample platform 38 by tensioning the biasing mechanism against rim 31. Biasing mechanism 84 is shown coupled to rim 31; however, alternative configurations are contemplated. For example, the biasing mechanism may be coupled to base 32 as well. Biasing mechanism 84 is shown as a pair of springs; however other mechanisms and/or configurations are contemplated. For example, rather than the one or more coiled springs suspending body 82 shown, one or more leaf springs supporting body 82 can be utilized.

Body 82 can be coupled to standoff 36 via footing 72, and wall 74 of standoff 36 can connect footing 72 to cap 76 which is coupled to and/or supports platform 38. As can be seen, wall 74 is substantially thinner than body 82 to limit thermal conduction between body 82 and platform 38. Wall 74 and/or portions or the entirety of standoff 36 can be constructed of metal and/or organic materials such as aluminum and/or fiberglass composites. Standoff 36 can be insulative thereby thermally separating body 82 from platform 38. In accordance with example implementations, body 82 can be kept in thermodynamic equilibrium with the environment about the system. Body 82 can also be used as a large warm mass to facilitate experimental needs. For example, analytical components can be mounted to or thermodynamically connected with body 82 facilitating an even temperature between body 82 and the attachment.

Referring to FIG. 5, according to one embodiment, coldhead 50 can be received through base 32 and couple with thermal link 54 which couples with platform 38. Link 54 can be one or more copper strips, annealed for example. In this Figure, component 11 is shown with an additional support structure 52 such as an additional standoff that may be implemented as well.

In accordance with example implementations, a coldhead can be operationally coupled to the sample platform. Referring to FIG. 6, according to another embodiment coldhead 60 is provided through an opening 62 that may run continuously through standoff 36, assembly 34, and housing 30 to allow for operative coupling of head 60 with other components of the cryogenic system.

In accordance with the above systems, the sample platform, and/or the sample, can be insulated from both external temperatures and resonance frequencies. Accordingly, the support assembly can have a resonance frequency below 1.5 Hz attenuating mechanical energy above 1.5 Hz.

Referring to FIG. 7 In another embodiment, biasing mechanism 84 can be coupled to an assembly that can be adjusted in height, for optical alignment of platform 38 with the components mounted on the bench 12. For example, adjustment mechanism 70 can be provided that includes operable adjustment body 72 coupled to engagement body 74 that can be operably coupled to a biasing mechanism to raise/lower the sample platform.

Although some embodiments are shown to include certain features, the applicants specifically contemplate that any feature disclosed herein may be used together or in combination with any other feature on any embodiment of the invention. It is also contemplated that any feature may be specifically excluded from any embodiment of the invention.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

The invention claimed is:

1. A cryogenic sample analysis system comprising:
   a system housing in direct physical contact with an environment about the system;
   a sample platform within the system housing; and
   a resonance frequency insulating assembly operatively engaged between the sample platform and the housing, the frequency insulating assembly comprising a biasing mechanism suspending a weighted member, wherein the weighted member defines a mass larger than the mass of the sample platform.

2. The cryogenic sample analysis system of claim 1 wherein the biasing mechanism comprises one or more coiled springs.

3. The cryogenic sample analysis system of claim 2 wherein the weighted member is suspended from the system housing by the one or more springs.

4. The cryogenic sample analysis system of claim 1 wherein the biasing mechanism comprises one or more leaf springs.

5. The cryogenic sample analysis system of claim 4 wherein the weighted member is supported within the housing by the one or more leaf springs.

6. The cryogenic sample analysis system of claim 1 wherein the sample platform is operationally coupled to a coldhead.

7. The cryogenic sample analysis system of claim 6 further comprising an insulative wall about the coldhead.

8. The cryogenic sample analysis system of claim 6 further comprising insulative material between the sample platform and the resonance frequency insulating assembly, the coldhead extending through an opening within the insulative material.

9. The cryogenic sample analysis system of claim 8 wherein the insulative material supports the sample platform.

* * * * *

UNITED STATES PATENT AND TRADEMARK OFFICE
CERTIFICATE OF CORRECTION

| | | |
|---|---|---|
| PATENT NO. | : 10,451,529 B2 | Page 1 of 1 |
| APPLICATION NO. | : 15/456064 | |
| DATED | : October 22, 2019 | |
| INVENTOR(S) | : Caleb Schreibeis, Ben Linkenhoker and Luke Mauritsen | |

It is certified that error appears in the above-identified patent and that said Letters Patent is hereby corrected as shown below:

On the Title Page

(56) References Cited: page 2, 2nd column, 21st line:
Replace "Snow, U.S. Appl. No. 61/136,138, filed Aug. 14, 2009, titled"
With --Snow, U.S. Appl. No. 61/136,138, filed Aug. 14, 2008, titled--

Signed and Sealed this
Twenty-fourth Day of November, 2020

Andrei Iancu
*Director of the United States Patent and Trademark Office*